United States Patent
Sakoda et al.

(10) Patent No.: US 8,968,219 B2
(45) Date of Patent: Mar. 3, 2015

(54) MUSCLE TONUS MEASURING APPARATUS

(75) Inventors: Saburo Sakoda, Suita (JP); Toshimitsu Hamasaki, Suita (JP); Takuyuki Endo, Suita (JP)

(73) Assignee: Osaka University, Osaka (JP)

( * ) Notice: Subject to any disclaimer, the term of this patent is extended or adjusted under 35 U.S.C. 154(b) by 311 days.

(21) Appl. No.: 13/696,440

(22) PCT Filed: May 9, 2011

(86) PCT No.: PCT/JP2011/060644
§ 371 (c)(1),
(2), (4) Date: Nov. 6, 2012

(87) PCT Pub. No.: WO2011/145465
PCT Pub. Date: Nov. 24, 2011

(65) Prior Publication Data
US 2013/0053731 A1    Feb. 28, 2013

(30) Foreign Application Priority Data
May 17, 2010    (JP) ................................. 2010-113200

(51) Int. Cl.
*A61B 5/00*    (2006.01)

(52) U.S. Cl.
USPC .......................................................... 600/595

(58) Field of Classification Search
USPC ......................................... 600/546, 587, 595
See application file for complete search history.

(56) References Cited

U.S. PATENT DOCUMENTS

| | | | |
|---|---|---|---|
| 5,911,693 A | 6/1999 | Prochazka et al. | |
| 6,596,066 B2* | 7/2003 | Lye et al. | 106/31.47 |
| 7,125,388 B1* | 10/2006 | Reinkensmeyer et al. | 601/5 |
| 7,433,733 B2* | 10/2008 | Endo et al. | 600/546 |
| 8,246,555 B2* | 8/2012 | Chiu et al. | 600/595 |
| 8,523,741 B2* | 9/2013 | Chiu et al. | 482/8 |
| 8,790,258 B2* | 7/2014 | Stark et al. | 600/301 |
| 2011/0087128 A1 | 4/2011 | Sakoda et al. | |

FOREIGN PATENT DOCUMENTS

WO    2009/154117    12/2009

OTHER PUBLICATIONS

Endo, et al., "Development of quantitative measurement system for diagnosis of Parkinson's disease", Sōgōrinshō, Dec. 2010, vol. 59, No. 12, with an English translation—11 pages.

(Continued)

*Primary Examiner* — Max Hindenburg
(74) *Attorney, Agent, or Firm* — Hamre, Schumann, Mueller & Larson, P.C.

(57) ABSTRACT

A detection unit (10) detects a joint angle and a joint torque for causing the joint of a subject (1) to undergo passive flexion and extension movement, and an arithmetic unit (50) performs arithmetic processing on an output signal from the detection unit. The arithmetic unit divides the relationship between the joint torque and the joint angle in at least one of the extension phase and the flexion phase into two or more portions including a proximal-side portion and a distal-side portion according to a joint angle, and obtains the elastic coefficient of the joint from the relationship between the joint torque and the joint angle in at least one of the distal-side portion and the proximal-side portion. This enables distinguishing between a healthy subject and a Parkinson's disease patient with a simple configuration, without the measurement of surface myoelectric potential.

7 Claims, 9 Drawing Sheets

(56) References Cited

OTHER PUBLICATIONS

Endo, et al., "Systematic analysis of muscle tonus abnormality with dynamic system identification approach", Journal of the Society of Biomechanisms, 2010, vol. 34, No. 2, with an English translation—17 pages.

Endo, et al., "A Novel Method for Systematic Analysis of Rigidity in Parkinson's Disease", Movement Disorders, 2009, pp. 1-7.

Prochazka, et al., "Measurement of rigidity in Parkinson's disease", Movement Disorders, vol. 12, No. 1, Jan. 1997, pp. 24-32.

Ju, et al., "Time-course analysis of stretch reflexes in hemiparetic subjects using an on-line spasticity measurement system", Journal of Electromyography and Kinesiology, vol. 10, No. 1, Feb. 2000, pp. 1-14.

Nuyens, et al., "Torque variations during repeated passive isokinetic movements of the knee in subjects with Parkinson's disease and healthy control subjects", Parkinsonism and Related Disorders, vol. 6, No. 2, Apr. 2000, pp. 87-93.

Kondraske, et al, "A Computer-based System for Automated Quantitation of Neurologic Function", IEEE Transactions on Biomedical Engineering, vol. BME-31, No. 5, May, 1984, pp. 401-414.

Fung, et al., "Objective Quantification of Resting and Activated Parkinsonian Rigidity: A Comparison of Angular Impulse and Work Scores", Movement Disorders, vol. 15, No. 1, Jan. 2000, pp. 48-55.

\* cited by examiner

FIG. 7

MUSCLE TONUS MEASURING APPARATUS

TECHNICAL FIELD

The present invention relates to a muscle tonus measuring apparatus for measuring muscle tonus characteristics of Parkinson's disease patients and stroke patients, and objectively evaluating the muscle tonus characteristics.

BACKGROUND ART

Abnormalities of muscle tonus caused by neuromuscular diseases are classified into spasticity and rigidity: the former is a pyramidal tract sign and the latter is an extrapyramidal sign. To detect the degree of those is quite important in neurological examination. However, it is difficult to evaluate the degree accurately unless a neurologist is experienced. Although the Modified Ashworth Scale for spasticity and the UPDRS (Unified Parkinson Disease Rating Scale) for muscle rigidity are known as evaluation indices that currently are used often in clinical trial, the criteria of both of them are semi-quantitative, and thus differences may arise between evaluators and with the same evaluator. Accordingly, the development of quantitative measuring devices for these is desired.

Patent Document 1 recites a muscle tonus measuring apparatus that causes the elbow joint of a subject to undergo passive flexion and extension movement, obtains an elastic coefficient for the elbow joint from the relationship between joint angle and joint torque, and measures the surface myoelectric potential of the biceps brachii muscle and the triceps brachii muscle at the same time. Patent Document 1 recites that a feature amount extracted from the elastic coefficient of the elbow joint and the surface myoelectric potentials is useful in identifying the severity of muscle rigidity in Parkinson's disease patients, and that a feature amount extracted from the surface myoelectric potential of the biceps brachii muscle is useful in distinguishing between a healthy subject and a Parkinson's disease patient.

PRIOR ART DOCUMENTS

Patent Document

Patent Document 1: WO 2009/154117 pamphlet

DISCLOSURE OF INVENTION

Problem to be Solved by the Invention

With the muscle tonus measuring system recited in the aforementioned Patent Document 1, measuring the elastic coefficient of the elbow joint allows the identification of the severity of muscle rigidity in a Parkinson's disease patient, but it is not possible to distinguish between a healthy subject and a Parkinson's disease patient. Distinguishing between a healthy subject and a Parkinson's disease patient requires the separate measurement of surface myoelectric potential.

An object of the present invention is to provide a muscle tonus measuring apparatus with a simple configuration that can distinguish between a healthy subject and a Parkinson's disease patient without the measurement of surface myoelectric potential.

Means for Solving Problem

A muscle tonus measuring apparatus of the present invention includes a detection unit that detects a joint torque of a subject for causing the joint to undergo passive flexion and extension movement and a joint angle, and an arithmetic unit that performs arithmetic processing on an output signal from the detection unit. The arithmetic unit divides a relationship between the joint torque and the joint angle in at least one of an extension phase and a flexion phase into two or more portions including a proximal-side portion and a distal-side portion according to a joint angle, and obtains an elastic coefficient of the joint from the relationship between the joint torque and the joint angle in at least one of the distal-side portion and the proximal-side portion.

Effects of the Invention

According to a muscle tonus measuring apparatus of the present invention, an objective indicator for distinguishing between a healthy subject and a Parkinson's disease patient without the measurement of surface myoelectric potential can be provided at low cost with a method similar to clinical examination techniques that conventionally have been performed by physicians in clinical examinations.

DESCRIPTION OF THE INVENTION

In the above-described muscle tonus measuring apparatus of the present invention, it is preferable that the arithmetic unit divides the relationship between the joint torque and the joint angle in the extension phase into two or more portions including the proximal-side portion and the distal-side portion according to a joint angle, and obtains a distal elastic coefficient in the extension phase of the joint from the relationship between the joint torque and the joint angle in the distal-side portion. Accordingly, it is possible to distinguish between a healthy subject and a Parkinson's disease patient using only the distal elastic coefficient in the extension phase, thus enabling further simplified arithmetic processing.

In the above configuration, the arithmetic unit may further obtain the proximal elastic coefficient in the extension phase of the joint from the relationship between the joint torque and the joint angle in the proximal-side portion.

Alternatively, the arithmetic unit may divide the relationship between the joint torque and the joint angle in each of the extension phase and the flexion phase into two or more portions including the proximal-side portion and the distal-side portion according to a joint angle, and obtain a proximal elastic coefficient in the extension phase and a distal elastic coefficient in the extension phase of the joint from the relationship between the joint torque and the joint angle in the proximal-side portion and the distal-side portion in the extension phase; a proximal elastic coefficient in the flexion phase and a distal elastic coefficient in the flexion phase of the joint from the relationship between the joint torque and the joint angle in the proximal-side portion and the distal-side portion in the flexion phase; a full-range elastic coefficient in the extension phase of the joint in a range including the distal-side portion and the proximal-side-portion, from the relationship between the joint torque and the joint angle in the extension phase; and a full-range elastic coefficient in the flexion phase of the joint in a range including the distal-side portion and the proximal-side portion, from the relationship between the joint torque and the joint angle in the flexion phase. This enables distinguishing between a healthy subject and a Parkinson's disease patient even when using the proximal, distal, and full-range elastic coefficient in the extension phase, and the proximal, distal, and full-range elastic coefficient in the flexion phase.

It is preferable that the joint angle between the proximal-side portion and the distal-side portion is in a range of 59 degrees to 63 degrees inclusive.

It is preferable that the arithmetic unit divides the relationship between the joint torque and the joint angle into two portions according to a joint angle, the two portions being the proximal-side portion and the distal-side portion. It is possible to distinguish between a healthy subject and a Parkinson's disease patient with the simple technique of dividing the relationship between the joint torque and the joint angle into two portions according to a joint angle. In this case, the joint angle for dividing the relationship into the proximal-side portion and the distal-side portion is preferably in the range of 59 degrees to 63 degrees inclusive, or more preferably is 60 degrees.

The arithmetic unit may further obtain a sum of bias differences that is obtained by calculating differences between the joint torque in the flexion phase and the joint torque in the extension phase (bias difference) for a plurality of joint angles, and adding together the differences. This further enables identifying the severity of muscle rigidity (UPDRS 1 to 4) in a Parkinson's disease patient.

It is preferable that the joint is an elbow joint. This enables objectively distinguishing between a healthy subject and a Parkinson's disease patient with a method similar to clinical examination techniques that have been performed conventionally by physicians in clinical examinations.

Below, the present invention will be described in detail while disclosing a preferred embodiment. However, it goes without saying that the present invention is not limited to the following embodiment. For the sake of convenience in the description, the drawings that are referenced in the following description show simplifications of among the constituent members of the embodiment of the present invention, only relevant members that are necessary for describing the present invention. The present invention therefore can include arbitrary constituent members that are not shown in the following drawings. Also, regarding the dimensions of the members in the drawings, the dimensions of the actual constituent members, the ratios of the dimensions of the members, and the like are not shown faithfully.

Figure 1:
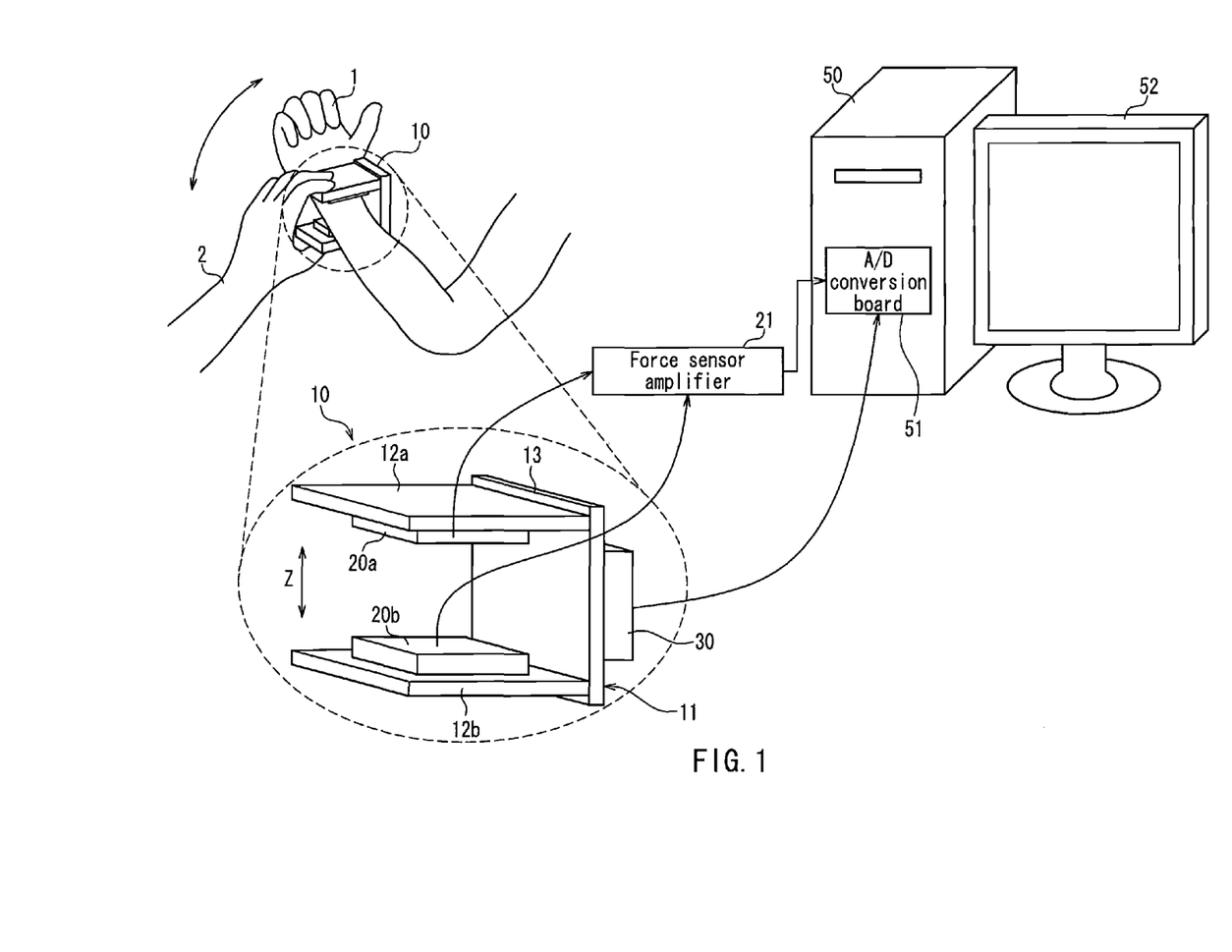
FIG. 1 is a diagram showing a schematic configuration of a muscle tonus measuring apparatus according to an embodiment of the present invention.

FIG. 1 shows the schematic configuration of a muscle tonus measuring apparatus for measuring muscle tonus characteristics through flexion and extension movements of an elbow joint of a patient, according to an embodiment of the present invention.

This muscle tonus measuring apparatus includes a detection unit 10 that detects the joint torque of the elbow joint for causing the elbow joint of a subject 1 to undergo passive flexion and extension movement and the joint angle of the elbow joint, and an arithmetic unit 50 that performs arithmetic processing on an output signal from the detection unit 10. As shown in FIG. 1, the detection unit 10 is fitted so as to sandwich the wrist joint portion of the subject 1, and an examiner 2 flexes and extends the elbow joint of the subject 1 via the detection unit 10.

The detection unit 10 includes a base 11 that has a substantially square-cornered U shape or is substantially U-shaped and can be considered to be a substantially rigid body.

A pair of force sensors 20a and 20b are fixed so as to oppose each other on a pair of sandwich plates 12a and 12b of the base 11 that oppose each other. The structure of the force sensors 20a and 20b is not limited as long as compressive force applied to the force sensors 20a and 20b can be detected, and general-purpose force sensors that are conventionally known can be used as the force sensors 20a and 20b, for example. If the direction in which the pair of force sensors 20a and 20b are in opposition is the Z axis, the force sensors 20a and 20b detect at least force in the Z axis direction. For example, general-purpose small triaxial force sensors that detect forces in three axial directions including the Z axis can be used as the force sensors 20a and 20b. By detecting forces in the orthogonal biaxial directions that are orthogonal to the Z axis direction in addition to force in the Z axis direction, the direction of the force applied to the subject 1 by the examiner 2 can be revised, and data on the detected force in the Z axis direction can be corrected. In order to alleviate discomfort due to the force sensors 20a and 20b being in direct contact with the skin of the subject 1 when causing flexion and extension movements of the elbow joint, soft pads may be attached to the mutually opposing faces of the force sensors 20a and 20b (the faces brought into contact with the wrist joint portion of the subject 1).

A gyroscope 30 is fixed on a bridge plate 13 that connects the pair of sandwich plates 12a and 12b of the base 11. The gyroscope 30 detects changes in the orientation of the detection unit 10 in which the gyroscope 30 is included, which changes following flexion and extension movements of the elbow joint of the subject 1.

When the elbow joint of the subject 1 is caused to undergo flexion and extension movement, the detection unit 10 moves along a circular arc with the elbow joint serving as the center. During flexion and extension movements of the elbow joint, the orientation of the detection unit 10 is maintained such that the Z axis is always parallel to the tangential direction of this circular arc. The force sensors 20a and 20b output a voltage according to the force in the Z axis direction applied by the examiner 2 to the subject 1 when the examiner 2 causes the elbow joint of the subject 1 to undergo flexion and extension movements. The voltage output from the force sensors 20a and 20b is amplified by a force sensor amplifier 21 as necessary, and thereafter is input to the arithmetic unit 50 via an A/D conversion board 51. The voltage output from the gyroscope 30 according to change in the orientation thereof is input to the arithmetic unit 50 via the A/D conversion board 51.

For example, a general-purpose personal computer can be used as the arithmetic unit 50. An output apparatus 52 may be connected to the arithmetic unit 50. For example, any of various displays and printers can be used as the output apparatus 52.

Figure 2:
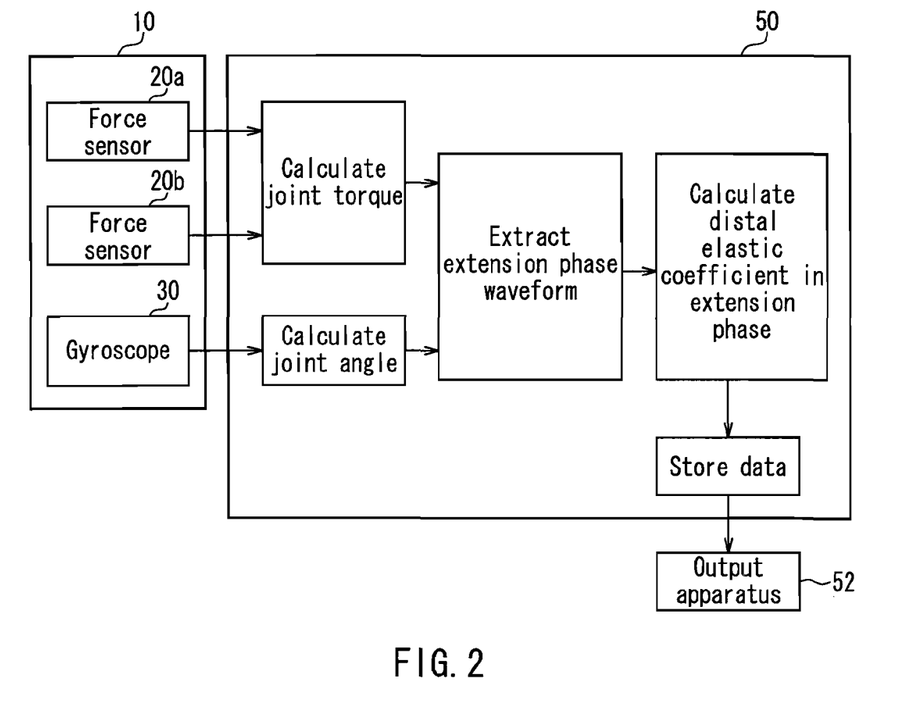
FIG. 2 is a diagram showing a data analysis technique in the muscle tonus measuring apparatus according to the embodiment of the present invention.

FIG. 2 is a diagram showing a technique of data analysis performed by the arithmetic unit 50 in the muscle tonus measuring apparatus according to the present embodiment.

A joint torque and a joint angle of the elbow joint of the subject 1 are measured while repeating four phases, namely (1) a maximal extension static phase, (2) a dynamic flexion phase, (3) a maximal flexion static phase, and (4) a dynamic extension phase.

The joint torque is calculated based on the force in the Z axis direction detected via the force sensors 20a and 20b, and the distance between the elbow joint of the subject 1 and the position where the detection unit 10 is fitted (i.e., the radius of the circular arc along which the detection unit 10 moves in the flexion and extension movements), which has been measured separately. The joint angle is calculated by integrating the change in the orientation (angular velocity) of the detection unit 10 detected via the gyroscope 30.

Change over time (a waveform) in the relationship between the joint torque and the joint angle in the dynamic extension phase in particular is extracted from change over time (raw waveforms) in the joint torque and the joint angle when the four phases are repeated. Furthermore, the relationship between the joint torque and the joint angle in the dynamic extension phase is divided into two portions, namely a proximal-side (flexion-side) portion and a distal-side (extension-side) portion, according to a joint angle, and the elastic coefficient of the elbow joint (distal elastic coefficient in the extension phase) is calculated from the relationship between the joint torque and the joint angle in the distal-side dynamic extension phase. The elastic coefficient can be obtained from the slope of the regression line of the graph (waveform) indicating the relationship between the joint torque and the joint angle.

Data regarding the distal elastic coefficient in the extension phase obtained by the arithmetic unit 50 may be stored in the arithmetic unit 50. Also, the arithmetic unit 50 may analyze the stored data with a statistical technique, for example. A raw waveform diagram indicating change over time in the joint angle and the joint torque, the results of the calculation of the distal elastic coefficient in the extension phase, the results of a comparison between a measured distal elastic coefficient in the extension phase and stored data, the results of an UPDRS evaluation, and the like are output to the output apparatus 52 in accordance with a request from the examiner.

With the muscle tonus measuring apparatus recited in Patent Document 1 described above, a full-range elastic coefficient in the dynamic extension phase and a full-range elastic coefficient in the dynamic flexion phase are calculated from the relationship between the joint torque and the joint angle in the dynamic extension phase and the dynamic flexion phase in the joint angle range of 10 degrees to 110 degrees. In other words, this is based on the idea that there is one elastic coefficient for each of the dynamic extension phase and the dynamic flexion phase in this joint angle range. Although such elastic coefficients demonstrate a good correlation with the UPDRS rigidity score, which is a scale for the clinical assessment of Parkinson's disease, it has not been possible to distinguish between a healthy subject (UPDRS 0) and a Parkinson's disease patient who has a slight amount of muscle rigidity (UPDRS 1).

In view of this, as a result of detailed examination of change over time in the relationship between the joint torque and the joint angle in the dynamic extension phase and the dynamic flexion phase, the inventors of the present invention found that a healthy subject in particular does not have one elastic coefficient in the dynamic extension phase and the dynamic flexion phase, but rather has different elastic coefficients in the proximal side and the distal side, the boundary between which is in the vicinity of the joint angle of 60 degrees. Then, as a result of examination of the relationship between UPDRS rigidity scores and proximal-side and distal-side elastic coefficients in the dynamic extension phase and the dynamic flexion phase, it was found that it is possible to distinguish between a healthy subject and a Parkinson's disease patient by using the distal-side elastic coefficient in the dynamic extension phase (distal elastic coefficient in the extension phase), and the present invention was achieved. The technique of performing analysis on characteristics of joint movement that have been divided into a proximal-side portion and a distal-side portion according to a joint angle is unprecedented.

The inventors of the present invention also found that it is possible to distinguish between a healthy subject and a Parkinson's disease patient even when using a total of six elastic coefficients, namely the proximal-side, distal-side, and full-range elastic coefficients in the dynamic extension phase, and the proximal-side, distal-side, and full-range elastic coefficients in the dynamic flexion phase. Here, "full-range" refers to the joint angle range in the dynamic extension phase and the dynamic flexion phase before the division into a proximal side portion and a distal side portion.

According to the present invention, distinguishing between a healthy subject and a Parkinson's disease patient does not require the measurement of surface myoelectric potential, which is necessary in Patent Document 1. If the distal elastic coefficient in the extension phase (or the aforementioned six elastic coefficients) obtained with the present invention is used with at least one of the bias difference and the elastic coefficients in the dynamic extension phase and the dynamic flexion phase (full-range elastic coefficient in the extension phase and the full-range elastic coefficient in the flexion phase) recited in Patent Document 1, it is possible to provide an objective evaluation of all scores from UPDRS 0 to 4 with an apparatus that has the simple configuration shown in FIG. 1 that omits the use of a surface myoelectric potentiometer.

The joint angle for division into a proximal side portion and a distal side portion is not particularly limited, but is preferably in the range of 59 degrees to 63 degrees inclusive, or more preferably is 60 degrees. This enables more accurate distinguishing between a healthy subject and a Parkinson's disease patient.

The present invention is not limited to the above embodiment or the following examples, and various modifications can be made.

For example, the shape of the base where the force sensors 20a and 20b and the gyroscope 30 are mounted does not need to be a substantially square-cornered U shape or substantially U-shaped as in the above embodiment, and for example, the overall shape thereof may be any of a circle, an ellipse and various polygons including a quadrangle, for instance, or may be a toroidal shape with a through-hole in the center. Furthermore, for the purpose of improving the fit to a subject, the base may have a movable portion, or part of the base or the entire base may have flexibility.

Instead of the pair of force sensors 20a and 20b, a single force sensor for detecting pushing and pulling forces applied when the examiner 2 causes the elbow joint of the subject 1 to undergo flexion and extension movement may be used.

A stage for supporting the subject's joint may be provided, and a distance sensor for automatically measuring the distance between this stage and the detection unit 10 may further be provided. Accordingly, the turning radius of the detection unit 10 necessary for calculating a joint torque can be measured easily.

In the above embodiment, the gyroscope 30 for measuring a joint angle is mounted on the base 11 together with the force sensors 20a and 20b. Accordingly, the entire apparatus can be reduced in size, and a joint torque and a joint angle can be simultaneously measured by merely fitting the detection unit 10 around the subject. However, in the present invention, the method for measuring a joint angle is not limited to this, and a known angular change measurement method can be utilized. For example, separately from the detection unit 10 including the force sensors 20a and 20b, a sensor for angle measurements (for example, a potentiometer or a rotary encoder) may be fitted in the vicinity of a joint of the subject via a jig.

The arithmetic unit for performing predetermined arithmetic processing using measured data and the display apparatus for displaying an arithmetic result may be reduced in size and mounted on the detection unit 10.

It is of course possible to apply the measuring apparatus of the present invention to joints other than the elbow joint (e.g., a wrist or a knee joint). The shape of the detection unit 10 can be changed appropriately depending on the joint to which it is applied.

The apparatus of the present invention may be used to further obtain the proximal-side elastic coefficient in the dynamic extension phase (proximal elastic coefficient in the extension phase) in addition to the distal elastic coefficient in the extension phase. For example, if the distal elastic coefficient in the extension phase and the proximal elastic coefficient in the extension phase are compared, it is possible to evaluate whether the elastic coefficient in the extension phase is made up of two different elastic coefficients on the distal side and the proximal side, or made up of one elastic coefficient that has no difference between the two sides. It is possible for the result of this evaluation to be used as supplementary data when objectively distinguishing between a healthy subject and a Parkinson's disease patient using the distal elastic coefficient in the extension phase.

Furthermore, the apparatus of the present invention may be used to calculate a feature amount such as the full-range elastic coefficient in the dynamic flexion phase, the full-range elastic coefficient in the dynamic extension phase, and the sum of bias differences, which are recited in Patent Document 1. This enables objectively identifying the severity of muscle rigidity in a Parkinson's disease patient.

Here, "sum of bias differences" is obtained as described below. In the joint angle-torque variation curve obtained by causing the joint to undergo flexion and extension movement (e.g., see later-described FIG. 4), the "bias difference" for a certain joint angle is the result of obtaining the difference between the average value of torque in all measurements in the dynamic flexion phase (dynamic flexion phase bias) and the average value of torque in all measurements in the dynamic extension phase (dynamic extension phase bias). The bias difference is calculated for multiple joint angles, and the calculated bias differences are added together to obtain the "sum of bias differences". It is preferable that the joint angles at which the bias difference is obtained include a distal-side angle (e.g., 30°), a proximal-side angle (e.g., 90°), and the angle between the distal side and the proximal side (e.g., 60°).

Also, a torque differential value may be calculated by performing temporal differentiation on joint torque in the dynamic flexion phase and/or the dynamic extension phase as recited in Patent Document 1. This torque differential value can be used as supplementary data when objectively distinguishing between a healthy subject and a Parkinson's disease patient using the distal elastic coefficient in the extension phase (or the six elastic coefficients described above). This also enables objectively distinguishing between the presence and absence of tremors in a Parkinson's disease patient.

In the above description, the relationship between the joint torque and the joint angle in the dynamic extension phase and the dynamic flexion phase is divided into two portions, namely the proximal-side portion and the distal-side portion, according to the joint angle, but the present invention is not limited to this, and the relationship may be divided into three or more portions including the proximal-side portion and the distal-side portion. For example, a configuration is possible in which the joint angle range of the proximal-side portion and the joint angle range of the distal-side portion are separated from each other instead of being continuous with each other.

Although the example of distinguishing between a healthy subject and a Parkinson's disease patient using the distal elastic coefficient in the extension phase is described above, the present invention is not limited to this. Specifically, depending on the joint that is caused to undergo flexion and extension movement, it is possible to be able distinguish between a healthy subject and a Parkinson's disease patient using any one among the proximal elastic coefficient in the flexion phase, the distal elastic coefficient in the flexion phase, the proximal elastic coefficient in the extension phase, and the distal elastic coefficient in the extension phase.

In Examples 1 and 2 described below, the flexion phase and the extension phase are obtained after extracting a portion corresponding to the joint angle range of 10 to 110 degrees from a raw waveform diagram of the joint torque and the joint angle obtained when causing a joint to undergo flexion and extension movement, but the joint angle range of the flexion phase and the extension phase is not limited to 10 degrees to 110 degrees. The lower limit value and the upper limit value of the joint angle range of the flexion phase and the extension phase may be greater or less than the above values. This joint angle range may be changed appropriately according to the subject and the joint that is caused to undergo flexion and extension movement. Furthermore, the angle ranges of the distal-side portion and the proximal-side portion also can be changed appropriately.

EXAMPLE 1

Object

As described above, with a healthy subject, the elastic coefficients in the passive dynamic extension phase and dynamic flexion phase take different values on the proximal side and the distal side. In view of this, the optimum joint angle was obtained for dividing the elastic coefficients in the dynamic extension phase and dynamic flexion phase for a healthy subject into a proximal-side portion and a distal-side portion.

<Measurement>

The muscle tonus measuring apparatus shown in FIG. 1 was used to measure the joint angle and the joint torque for both elbow joints of 20 healthy subjects (15 men and 5 women, aged 55 to 85).

The subjects were instructed to remain relaxed resting in a sitting position, and the examiner caused the elbow joint of each subject to undergo passive flexion and extension movement while supporting the subject's elbow joint portion with one hand and holding the subject's wrist joint portion with the other hand via the detection unit 10. In the measurement, the elbow joint started at the maximal extension position and was held still for three seconds or more, then flexed to the maximal flexion position over two seconds and held still there for three or more seconds, and then extended to the maximal extension position over two seconds and held still there for three or more seconds, and this flexion and extension movement was repeated for 60 seconds. One session included four to five instances of this flexion and extension movement. This measurement was performed on each subject one or two times for both the left and right upper limbs, and thus data for 520 instances (260 instances of flexion and 260 instances of extension) was obtained with all of the subjects.

Figure 3:
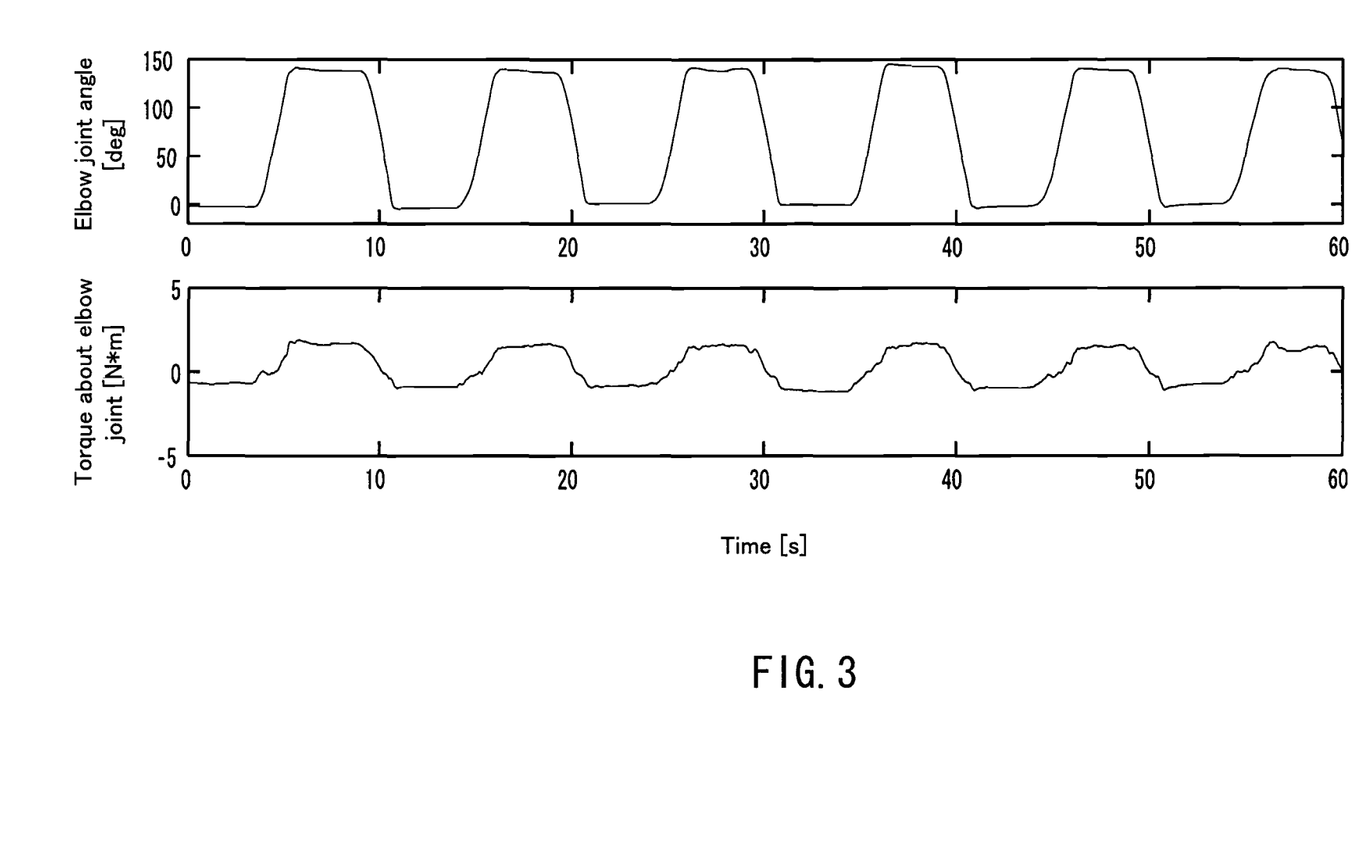
FIG. 3 is a representative raw waveform diagram of joint angles and joint torques for a healthy subject that are measured in Example 1.

FIG. 3 shows a raw waveform diagram of representative results of measuring the joint angle and the joint torque.

<Analysis>

The following analysis was performed on each data piece among the data (raw waveform diagram) for the 520 instances obtained in the aforementioned measurement.

Figure 4:
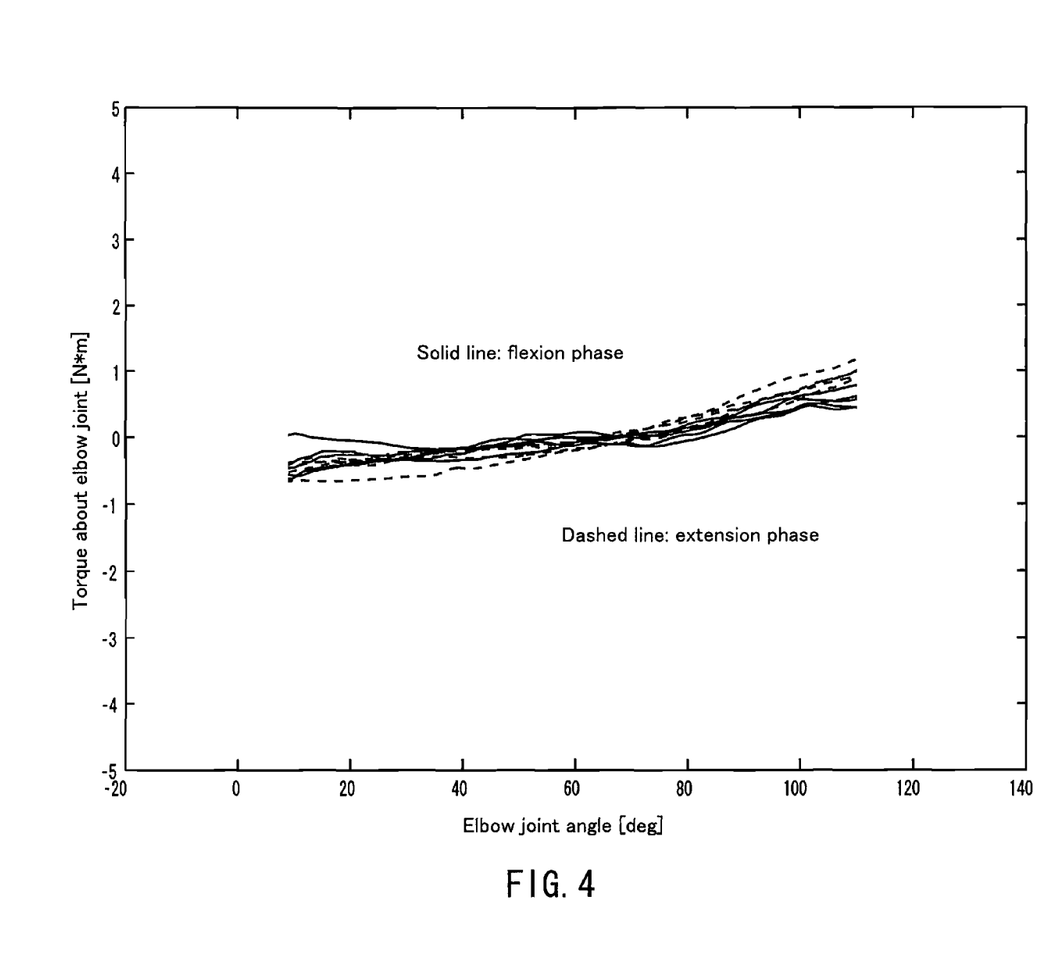
FIG. 4 shows joint angle-torque variation curves in a dynamic flexion phase and a dynamic extension phase that were obtained from the raw waveform diagram shown in FIG. 3.

First, a portion corresponding to the joint angle range of 10 to 110 degrees was extracted from the raw waveform diagram of FIG. 3 that was obtained in the aforementioned measurement, and joint angle-torque variation curves in the flexion phase and the extension phase such as those shown in FIG. 4 were obtained.

For both the flexion phase and the extension phase, the optimal angle (dividing angle) for dividing the joint angle-torque variation curves was obtained, and that optimal angle was used to obtain a regression line for the joint angle-torque variation curves in the proximal-side portion and the distal-side portion. This calculation was performed using a likelihood-maximizing method.

In the case where the p value of the likelihood ratio test satisfies $p<0.05$, approximating the joint angle-torque variation curve in the joint angle range of 10 to 110 degrees by two regression lines was determined to be more preferable than approximating it by one regression line, and the curve was considered to be "significant example".

A 95% confidence interval was then obtained for the dividing angle of the "significant example".

<Results>

The results are shown organized in Table 1.

TABLE 1

| Significant examples in all sessions | Significant examples in flexion phase | Flexion phase dividing angle (95% confidence interval) | Significant examples in extension phase | Extension phase dividing angle (95% confidence interval) |
|---|---|---|---|---|
| 520/520 (100%) | 260/260 (100%) | 58.1° (55.3°-60.9°) | 260/260 (100%) | 61.1° (59.2°-62.9°) |

As shown in Table 1, the results obtained for all of the pieces of data on the 520 instances for healthy subjects indicated that it is preferable that the joint angle-torque variation curves are approximated by two regression lines in both the flexion phase and the extension phase. The dividing angles in this case were 58.1 degrees for the flexion phase and 61.1 degrees for the extension phase. In both the flexion phase and the extension phase, the angle of 60 degrees was included in the 95% confidence interval for the dividing angle. Accordingly, there is no problem with setting the dividing angle to 60 degrees for both the flexion phase and the extension phase.

EXAMPLE 2

Object

The extent of correlation with UPDRS rigidity scores was investigated for proximal-side and distal-side elastic coefficients obtained when dividing joint angle-torque variation curves in the dynamic extension phase and the dynamic flexion phase into two portions using the dividing angle of 60 degrees that was obtained in Example 1.

<Measurement>

With respect to 24 patients diagnosed as having Parkinson's disease based on Parkinson's disease diagnostic criteria (1995) by the research study group of specified diseases and neurodegenerative diseases of the Ministry of Health and Welfare (17 men and 7 women, aged 47 to 85), and the above-described 20 healthy subjects in Example 1 (15 men and 5 women, aged 55 to 85), the joint angle and the joint torque were measured using the muscle tonus measuring apparatus shown in FIG. 1.

Prior to the measurement, the healthy subjects underwent neurological examination, and the Parkinson's disease patients were assessed using UPDRS (Unified Parkinson Disease Rating Scale) Part III, and muscle rigidity was given a score in 5 levels from 0 to 4 (see Table 2).

TABLE 2

Muscle rigidity scores
(Patient at rest. Determine based on main joints.
Cogwheel phenomenon not recorded.)

0: Absent.
1: Slight or inducible by mirror movement or other movements.
2: Mild to moderate muscle rigidity.
3: Marked muscle rigidity, but range of joint motion is normal.
4: Severe muscle rigidity, and range of joint motion is limited.

The joint angle and the joint torque were measured using the same method as in Example 1 for the left and right upper limbs of the healthy subjects and the Parkinson's disease patients. At the same time, the surface myoelectric potential was measured with surface electrodes affixed at positions on the biceps brachii muscle and the triceps brachii muscle of the subjects. The data on healthy subjects clinically determined to have muscle rigidity and data considered to include obvious voluntary movement based on visual observation of an electromyogram were excluded from the 40 data pieces on the healthy subjects and the 48 data pieces on the Parkinson's disease patients, thus ultimately obtaining a total of 74 data pieces, namely 31 data pieces on healthy subjects and 43 data pieces on Parkinson's disease patients.

<Analysis>

The following analysis was performed on each of the aforementioned 74 data pieces.

First, the portion corresponding to the joint angle range of 10 to 110 degrees was extracted from the raw waveform diagram indicating joint angles and joint torques, and joint angle-torque variation curves in the flexion phase and the extension phase were obtained.

Then, a "full-range elastic coefficient in the flexion phase" was obtained from the slope of the regression line of the joint angle-torque variation curve in the flexion phase. Similarly, a "full-range elastic coefficient in the extension phase" was obtained from the slope of the regression line of the joint angle-torque variation curve in the extension phase.

Next, the joint angle-torque variation curve in the flexion phase was divided into two portions using the joint angle of 60 degrees, a "distal elastic coefficient in the flexion phase" was obtained from the slope of the regression line for the 10-degree to 60-degree portion, and a "proximal elastic coefficient in the flexion phase" was obtained from the slope of the regression line for the 60-degree to 110-degree portion. Similarly, the joint angle-torque variation curve in the extension phase was divided into two portions using the joint angle of 60 degrees, a "distal elastic coefficient in the extension phase" was obtained from the slope of the regression line for the 10-degree to 60-degree portion, and a "proximal elastic coefficient in the extension phase" was obtained from the slope of the regression line for the 60-degree to 110-degree portion.

Then, the correlation that the three types of elastic coefficients described above have with UPDRS rigidity scores was obtained for both the flexion phase and the extension phase.

Lastly, a test was performed between two groups, namely healthy subjects (UPDRS 0) and slight muscle rigidity (UPDRS 1).

<Results>

Figure 5A:
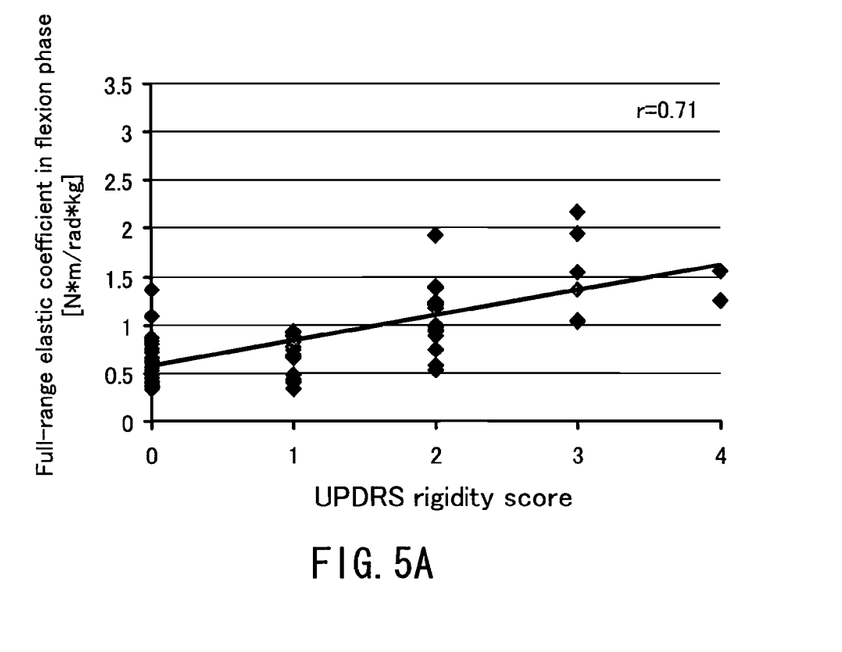
FIG. 5A is a diagram showing the relationship between UPDRS rigidity scores and full-range elastic coefficients in the flexion phase, which is obtained in Example 2.
Figure 5B:
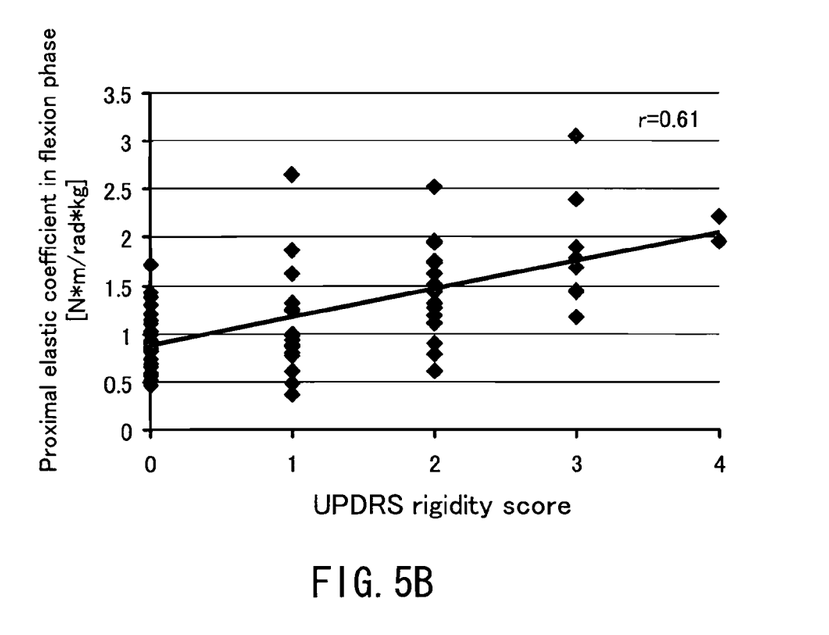
FIG. 5B is a diagram showing the relationship between UPDRS rigidity scores and proximal elastic coefficients in the flexion phase, which is obtained in Example 2.
Figure 5C:
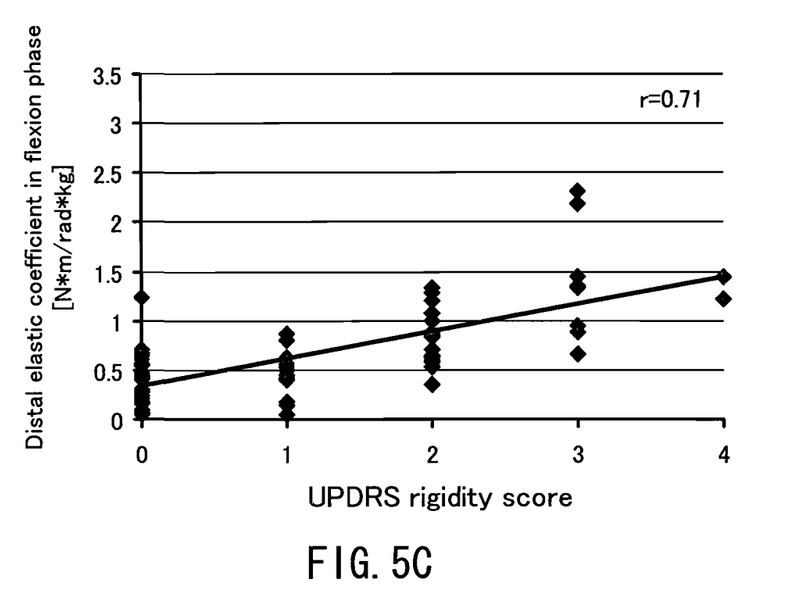
FIG. 5C is a diagram showing the relationship between UPDRS rigidity scores and distal elastic coefficients in the flexion phase, which is obtained in Example 2.

FIGS. 5A, 5B, and 5C show the relationships that the full-range, proximal, and distal elastic coefficients in the flexion phase have with UPDRS rigidity scores. In these figures, "r" denotes the coefficient of correlation with UPDRS rigidity scores. The full-range elastic coefficient and the distal elastic coefficient demonstrated approximately the same extent of good correlation with UPDRS rigidity scores. Also, no significant difference between UPDRS 0 and UPDRS 1 was observed in either case.

Figure 6A:
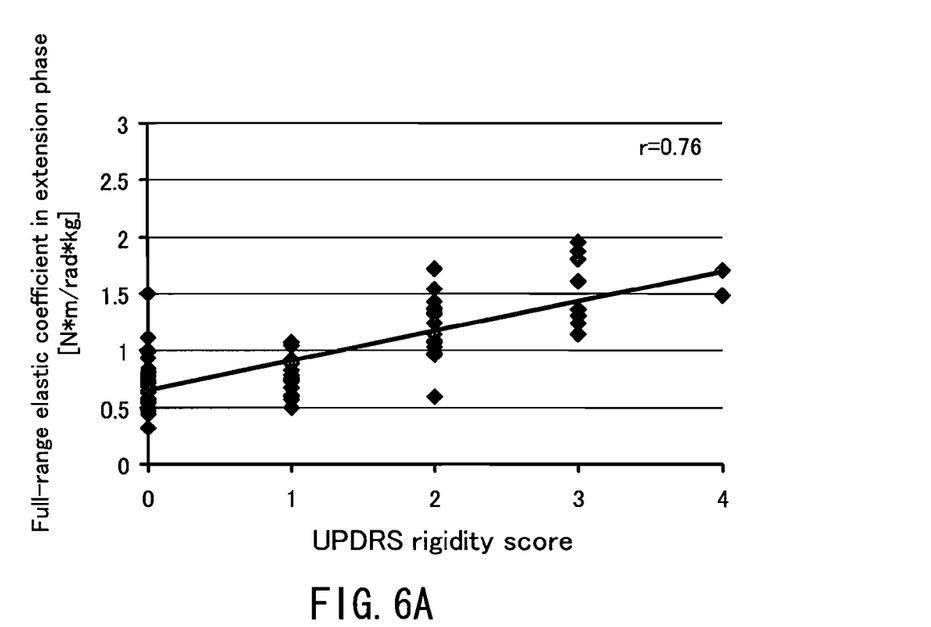
FIG. 6A is a diagram showing the relationship between UPDRS rigidity scores and full-range elastic coefficients in the extension phase, which is obtained in Example 2.
Figure 6B:
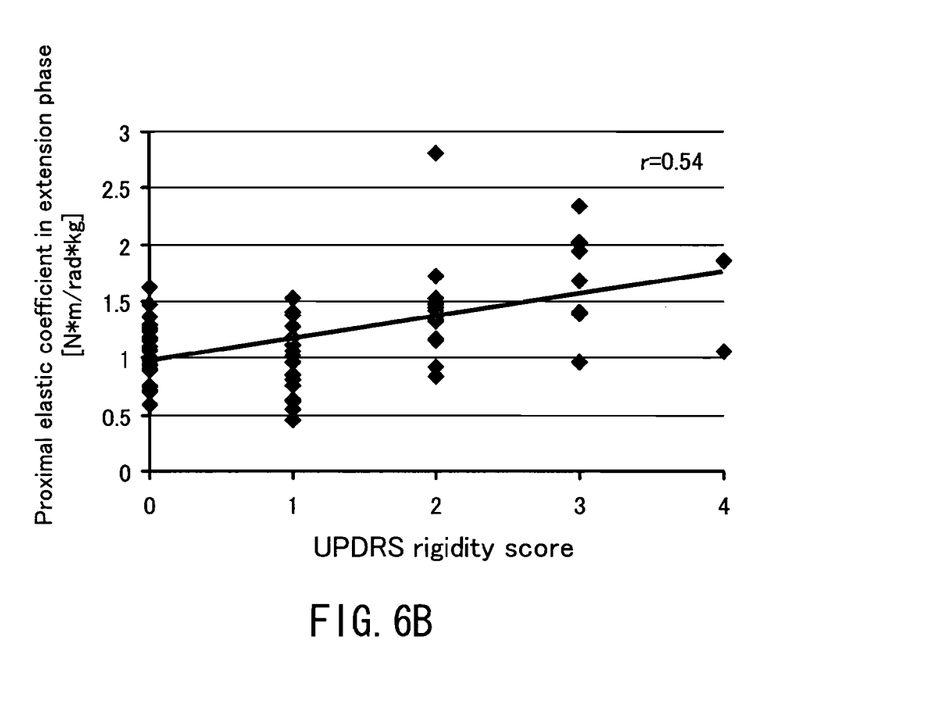
FIG. 6B is a diagram showing the relationship between UPDRS rigidity scores and proximal elastic coefficients in the extension phase, which is obtained in Example 2.
Figure 6C:
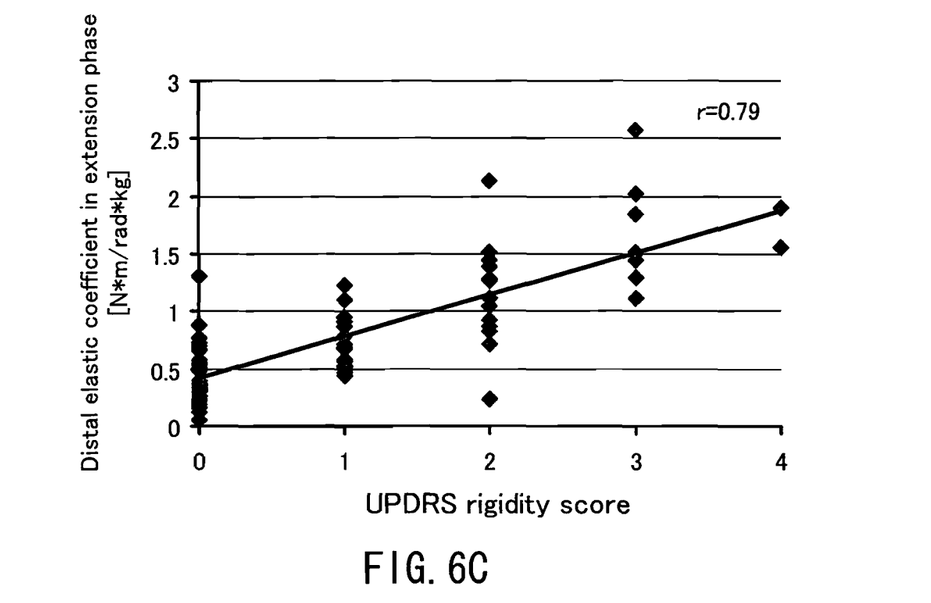
FIG. 6C is a diagram showing the relationship between UPDRS rigidity scores and distal elastic coefficients in the extension phase, which is obtained in Example 2.

FIGS. 6A, 6B, and 6C show the relationships that the full-range, proximal, and distal elastic coefficients in the extension phase have with UPDRS rigidity scores. In these figures, "r" denotes the coefficient of correlation with UPDRS rigidity scores. The distal elastic coefficient demonstrated the best correlation with UPDRS rigidity scores. Moreover, a significant difference between UPDRS 0 and UPDRS 1 was observed with the distal elastic coefficient ($p=0.0018$).

Figure 7:
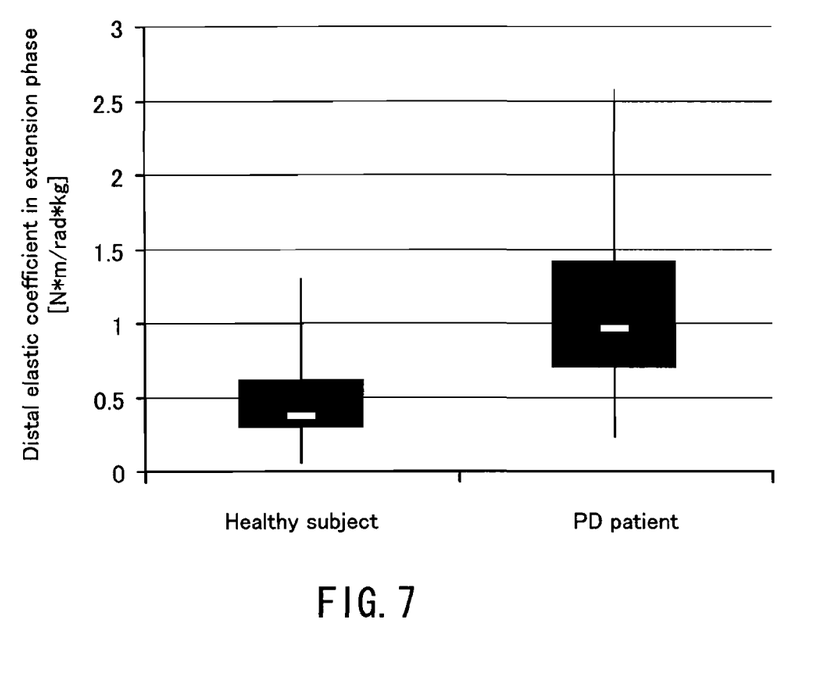
FIG. 7 is a box plot showing distal elastic coefficients in the extension phase that are obtained in Example 2, sorted according to healthy subjects and Parkinson's disease patients.

FIG. 7 is a box plot showing distal elastic coefficients in the extension phase sorted according to healthy subjects and Parkinson's disease patients (PD patients). Letting the cutoff value for the distal elastic coefficient in the extension phase be 0.50, a sensitivity of 91% and a specificity of 65% were observed, and the distal elastic coefficient in the extension phase was considered to be useful in distinguishing between a healthy subject and a Parkinson's disease patient.

Logistic discrimination was carried out taking into consideration the six elastic coefficients (the full-range elastic coefficient in the flexion phase, the distal elastic coefficient in the flexion phase, the proximal elastic coefficient in the flexion phase, the full-range elastic coefficient in the extension phase, the distal elastic coefficient in the extension phase, and the proximal elastic coefficient in the extension phase) and factors such as age, gender, and left/right side, and the obtained results indicated a sensitivity of 90.9%, a specificity of 81.3%, and a correct discrimination rate of 85.2% in the discrimination between a healthy subject and a Parkinson's disease patient. In other words, this suggested that a useful screening test can be performed when the full-range, proximal, and distal elastic coefficients in the flexion phase, and the full-range, proximal, and distal elastic coefficients in the extension phase are all used.

The embodiment and examples described above are all merely intended to clarify the technical content of the present invention, and the present invention is not to be interpreted as being limited to only such specific examples. Various modifications can be carried out within the spirit of the invention and the scope recited in the claims, and the present invention is intended to be interpreted broadly.

INDUSTRIAL APPLICABILITY

Although the utilization field of the present invention is not particularly limited, the present invention can be utilized over a wide range, such as the determination of the severity of Parkinson's disease, and the determination of therapeutic effects before and after antiparkinson drug administration.

DESCRIPTION OF REFERENCE NUMERALS

10 Detection unit
11 Base
12a,12b Sandwich plate
13 Bridge plate
20a,20b Force sensor
21 Force sensor amplifier
30 Gyroscope
50 Arithmetic unit
51 A/D conversion board
52 Output apparatus

The invention claimed is:

1. A muscle tonus measuring apparatus comprising:
a detection unit that detects a joint torque of a joint of a subject for causing the joint to undergo passive flexion and extension movement and a joint angle of the joint; and
an arithmetic unit that performs arithmetic processing on an output signal from the detection unit,
wherein the arithmetic unit divides a relationship between the joint torque and the joint angle in at least one of an extension phase and a flexion phase into two or more portions including a proximal-side portion and a distal-side portion according to a joint angle, and obtains an elastic coefficient of the joint from the relationship between the joint torque and the joint angle in at least one of the distal-side portion and the proximal-side portion.

2. The muscle tonus measuring apparatus according to claim 1, wherein the arithmetic unit divides the relationship between the joint torque and the joint angle in the extension phase into two or more portions including the proximal-side portion and the distal-side portion according to a joint angle, and obtains a distal elastic coefficient in the extension phase of the joint from the relationship between the joint torque and the joint angle in the distal-side portion.

3. The muscle tonus measuring apparatus according to claim 1,
wherein the arithmetic unit divides the relationship between the joint torque and the joint angle in each of the extension phase and the flexion phase into two or more portions including the proximal-side portion and the distal-side portion according to a joint angle, and obtains a proximal elastic coefficient in the extension phase and a distal elastic coefficient in the extension phase of the joint from the relationship between the joint torque and the joint angle in the proximal-side portion and the distal-side portion in the extension phase, a proximal elastic coefficient in the flexion phase and a distal elastic coefficient in the flexion phase of the joint from the relationship between the joint torque and the joint angle in the proximal-side portion and the distal-side portion in the flexion phase, a full-range elastic coefficient in the extension phase of the joint in a range including the distal-side portion and the proximal-side portion, from the relationship between the joint torque and the joint angle in the extension phase, and a full-range elastic coefficient in the flexion phase of the joint in a range including the distal-side portion and the proximal-side portion, from the relationship between the joint torque and the joint angle in the flexion phase.

4. The muscle tonus measuring apparatus according to claim 1, wherein the joint angle between the proximal-side portion and the distal-side portion is in a range of 59 degrees to 63 degrees inclusive.

5. The muscle tonus measuring apparatus according to claim 1, wherein the arithmetic unit divides the relationship between the joint torque and the joint angle into two portions according to a joint angle, the two portions being the proximal-side portion and the distal-side portion.

6. The muscle tonus measuring apparatus according to claim 1, wherein the arithmetic unit further obtains a sum of bias differences that is obtained by calculating differences between the joint torque in the flexion phase and the joint torque in the extension phase for a plurality of joint angles, and adding together the differences.

7. The muscle tonus measuring apparatus according to claim 1, wherein the joint is an elbow joint.

* * * * *